US012729369B2

(12) United States Patent
Trzonkowski et al.

(10) Patent No.: US 12,729,369 B2
(45) Date of Patent: Sep. 8, 2026

(54) PROCESS FOR MANUFACTURING OF ANTIGEN-SPECIFIC T LYMPHOCYTES

(71) Applicant: GDAŃSKI UNIWERSYTET MEDYCZNY, Gdańsk (PL)

(72) Inventors: Piotr Trzonkowski, Gdańsk (PL); Dorota Iwaszkiewicz-Grześ, Gdańsk (PL); Mateusz Gliwiński, Kwidzyn (PL)

(73) Assignee: GDANSKI UNIWERSYTET MEDYCZNY, Gdansk (PL)

( * ) Notice: Subject to any disclaimer, the term of this patent is extended or adjusted under 35 U.S.C. 154(b) by 901 days.

(21) Appl. No.: 17/635,755

(22) PCT Filed: Aug. 24, 2020

(86) PCT No.: PCT/PL2020/000073
§ 371 (c)(1),
(2) Date: Feb. 16, 2022

(87) PCT Pub. No.: WO2021/034208
PCT Pub. Date: Feb. 25, 2021

(65) Prior Publication Data

US 2022/0333072 A1 Oct. 20, 2022

(30) Foreign Application Priority Data

Aug. 22, 2019 (PL) ........................................ 430932

(51) Int. Cl.
*C12N 5/0783* (2010.01)
*C12N 13/00* (2006.01)

(52) U.S. Cl.
CPC ......... *C12N 5/0636* (2013.01); *C12N 5/0637* (2013.01); *C12N 5/0638* (2013.01); *C12N 13/00* (2013.01); *C12N 2500/02* (2013.01); *C12N 2501/33* (2013.01); *C12N 2501/998* (2013.01); *C12N 2502/1157* (2013.01)

(58) Field of Classification Search
None
See application file for complete search history.

(56) References Cited

U.S. PATENT DOCUMENTS

2019/0161728 A1 5/2019 Zagury et al.

FOREIGN PATENT DOCUMENTS

| | | | |
|---|---|---|---|
| JP | 2008-544760 | A | 12/2008 |
| JP | 2018-537964 | A | 12/2018 |
| WO | 2013131045 | A1 | 9/2013 |
| WO | 2018106885 | A1 | 6/2018 |
| WO | 2019-104875 | A1 | 6/2019 |

OTHER PUBLICATIONS

Jiang, Shuiping, et al. "Induction of allopeptide-specific human CD4+ CD25+ regulatory T cells ex vivo." Blood 102.6 (2003): 2180-2186. (Year: 2003).*

Salomon, Benoît, et al. "B7/CD28 costimulation is essential for the homeostasis of the CD4+ CD25+ immunoregulatory T cells that control autoimmune diabetes." Immunity 12.4 (2000): 431-440. (Year: 2000).*

Jarvinen, Lamis Z., et al. "CD154 on the surface of CD4+ CD25+ regulatory T cells contributes to skin transplant tolerance." Transplantation 76.9 (2003): 1375-1379. (Year: 2003).*

Geissmann, Frederic, et al. "Blood monocytes: distinct subsets, how they relate to dendritic cells, and their possible roles in the regulation of T-cell responses." Immunology and cell biology 86.5 (2008): 398-408. (Year: 2008).*

Veerapathran, Anandharaman, et al. "Ex vivo expansion of human Tregs specific for alloantigens presented directly or indirectly." Blood, The Journal of the American Society of Hematology 118.20 (2011): 5671-5680. (Year: 2011).*

Invitrogen user guide. CellTrace Cell Proliferation Kits. ThermoFisher Scientific. (Year: 2017).*

Lyons, A. Bruce, and Christopher R. Parish. "Determination of lymphocyte division by flow cytometry." Journal of immunological methods 171.1 (1994): 131-137. (Year: 1994).*

Andrés A: "Cancer incidence after immunosuppressive treatment following kidney transplantation." Crit Rev Oncol Hematol, 2005, pp. 71-85, vol. 56(1), doi: 10.1016/j.critrevonc.2004.11.010.

Barbaro MP, Spanevello A, Palladino GP, Salerno FG, Lacedonia D, Carpagnano GE: (2014). "Exhaled matrix metalloproteinase-9 (MMP-9) in different biological phenotypes of asthma." Eur J Intern Med., 2014, pp. 92-96, vol. 25(1), doi: 10.1016/j.ejim.2013.08.705.

Berney T, Secchi A: "Rapamycin in islet transplantation: friend or foe?" Transpl Int, 2009, pp. 153-161, vol. 22 (2), doi: 10.1111/j.1432-2277.2008.00743.x.

Bluestone JA, Buckner JH, Fitch M, Gitelman SE, Gupta S, Hellerstein MK, Herold KC, Lares A, Lee MR, Li K, Liu W, Long SA, Masiello LM, Nguyen V, Putnam AL, Rieck M, Sayre PH, Tang Q: "Type 1 diabetes immunotherapy using polyclonal regulatory T cells.", Sci Transl Med, 2015, 7(315): 315ra189, doi: 10.1126/scitranslmed.aad4134.

(Continued)

*Primary Examiner* — Tracy Vivlemore
*Assistant Examiner* — Fatimah Khalaf Matalkah
(74) *Attorney, Agent, or Firm* — Taro Yaguchi

(57) ABSTRACT

The invention relates to a new process for manufacturing in vitro antigen-specific T lymphocytes (CellTrAg), marked with intracellular dye and expanded in the presence of monocytes loaded with the antigen and subsequently sorted based on the low intensity of intracellular dye where the low intensity of fluorescence is a marker of antigen-specificity in that a loss of fluorescence correlated with the intensity of proliferation. The antigen specificity is assessed in functional tests in which antigen-specific lymphocytes sorted on the basis of low fluorescence are more active than non-specific lymphocytes with high fluorescence during sort; activity is defined in the case of regulatory T lymphocytes as inhibition of effector lymphocyte function and in the case of T effector lymphocytes as enhancing the characteristics of these cells such as proliferation, production of cytokines and cytotoxic factors.

6 Claims, 7 Drawing Sheets

(56) References Cited

OTHER PUBLICATIONS

Bluestone JA, Trotta E, Xu D: "The therapeutic potential of regulatory T cells for the treatment of autoimmune disease." Expert Opin Ther Targets, 2015, pp. 1091-1103, vol. 19(8), doi: 10.1517/14728222.2015.1037282.
Di Ianni M, Falzetti F, Carotti A, Terenzi A, Castellino F, Bonifacio E, Del Papa B, Zeit, Ostini RI, Cecchini D, Aloisi T, Perruccio K, Ruggeri L, Balucani C, Pierini A, Sportoletti P. Aristei C, Falini B, Reisner Y, Velardi A, Aversa F, Martelli MF: (2011). "Tregs prevent GVHD and promote immune reconstitution in HLA-haploidentical transplantation." Blood, 2011, pp. 3921-3928, vol. 117(14), doi: 10.1182/blood-2010-10-311894.
Fontenot JD, Gavin MA, Rudensky AY: "Foxp3 programs the development and function of CD4+CD25+ regulatory T cells." Nat Immunol, 2003, pp. 330-336, vol. 4(4), doi: 10.1038/ni904.
Gambineri E, Torgerson TR, Ochs HD: "Immune dysregulation, polyendocrinopathy, enteropathy, and X-linked inheritance (IPEX), a syndrome of systemic autoimmunity caused by mutations of FOXP3, a critical regulator of T-cell homeostasis." Curr Opin Rheumatol, 2003, pp. 430-435, vol. 15, doi: 10.1097/00002281-200307000-00010.
Geem D, Harusato A, Flannigan K, Denning TL, (2015). "Harnessing regulatory T cells for the treatment of inflammatory bowel disease." Inflamm Bowel Dis, 2015, pp. 1409-1418, 21(6), doi: 10.1097/MIB.0000000000000343.
Gupta S: "Immunotherapies in diabetes mellitus type 1." Med Clin North Am, 2012, pp. 621-634, vol. 96(3), doi: 10.1016/j.mcna.2012.04.008.
Hoffmann P. Boeld TJ, Eder R, Huehn J, Floess S, Wieczorek G, Olek S, Dietmaier W, Andreesen R, Edinger M: "Loss of FOXP3 expression in natural human CD4+CD25+ regulatory T cells upon repetitive in vitro stimulation." Eur J Immunol, 2009, pp. 1088-1097, vol. 39(4), doi: 10.1002/eji.200838904.
Krzystyniak A, Gołab K, Witkowski P, Trzonkowski P: (2014). "Islet cell transplant and the incorporation of Tregs." Curr Opin Organ Transplant, 2014, pp. 610-615, vol. 19(6), doi: 10.1097/MOT.0000000000000130.
Lima XT, Cintra ML, Piaza AC, Mamoni RL, Oliveira RT, Magalhães RF, Blotta MH: (2015). "Frequency and characteristics of circulating CD4(+) CD28(null) T cells in patients with psoriasis." Br J Dermatol, 2015, pp. 998-1005, vol. 173(4), doi: 10.1111/bjd.13993.
Malek TR: "The main function of IL-2 is to promote the development of T regulatory cells." J Leukoc Biol, 2003, pp. 961-965, vol. 74(6), doi: 10.1189/jlb.0603272.
Malek TR, Castro I: "Interleukin-2 receptor signaling: at the interface between tolerance and immunity." Immunity, 2010, pp. 153-165, vol. 33(2), doi: 10.1016/j.immuni.2010.08.004.
Marek-Trzonkowska N, Mysliwiec M, Dobyszuk A, Grabowska M, Techmanska I, Juscinska J, Wujtewicz MA, Witkowski P, Mlynarski W, Balcerska A, Mysliwska J, Trzonkowski P: "Administration of CD4+CD25highCD127-regulatory T cells preserves β-cell function in type 1 diabetes in children." Diabetes Care, 2021, pp. 1817-1820, vol. 35(9), https://doi.org/10.2337/dc12-0038.
Marek-Trzonkowska N, Mysliwec M, Siebert J, Trzonkowski P: "Clinical application of regulatory T cells in type 1 diabetes." Pediatr Diabetes, 2013, pp. 322-332, vol. 14(5), doi: 10.1111/pedi.12029.
Marek-Trzonkowska N, Mysliwiec M, Dobyszuk A, Grabowska M, Derkowska I, Juscinska J, Owczuk R, Szadkowska A, Witkowski P, Mlynarski W, Jarosz-Chobot P, Bossowski A, Siebert J, Trzonkowski P: "Therapy of type 1 diabetes with CD4(+)CD25(high)CD127-regulatory T cells prolongs survival of pancreatic islets—results of one year follow-up." Clin Immunol, 2014, pp. 23-30, vol. 153(1), doi: 10.1016/j.clim.2014.03.016.
Marek N, Bieniaszewska M, Krzystyniak A, Juścińska J, Myśliwska J, Witkowski P, Hellmann A, Trzonkowski P: "The time is crucial for ex vivo expansion of T regulatory cells for therapy." Cell Transplant, 2011, pp. 1747-1758, vol. 20(11-12), doi: 10.3727/096368911X566217.
Martelli MF, Di Ianni M, Ruggeri L, Falzetti F, Carotti A, Terenzi A, Pierini A, Massei MS, Amico L, Urbani E, Del Papa B, Zei T, Iacucci Ostini R, Cecchini D, Tognellini R, Reisner Y, Aversa F, Falini B, Velardi A: "HLA-haploidentical transplantation with regulatory and conventional T-cell adoptive immunotherapy prevents acute leukemia relapse." Blood, 2014, pp. 638-644, vol. 124(4), doi: 10.1182/blood-2014-03-564401.
Mu Q, Zhang H, Luo XM: "SLE: another autoimmune disorder influenced by microbes and diet?" Front Immunol, 2015, pp. 1-10, vol. 6:608, doi: 10.3389/fimmu.2015.00608.
Nishimura E, Sakihama T, Setoguchi R, Tanaka K, Sakaguchi S:, (2004). "Induction of antigen-specific immunologic tolerance by in vivo and in vitro antigen-specific expansion of naturally arising Foxp3+CD25+CD4+ regulatory T cells." Int Immunol, 2004, pp. 1189-1201, vol. 16(8), doi: 10.1093/intimm/dxh122.
Orent W, Mchenry AR, Rao DA, White C, Klein HU, Bassil R, Srivastava G, Replogle JM, Raj T, Frangieh M, Cimpean M, Cuerdon N, Chibnik L, Khoury SJ, Karlson EW, Brenner MN, De Jager P, Bradshaw EM, Elyaman W:, (2015). "Rheumatoid arthritis-associated RBPJ polymorphism alters memory CD4+ T cells." Hum Mol Genet, 2015, pp. 404-417, vol. 25(2), doi: 10.1093/hmg/ddv474.
Panettieri RA, Jr Covar R, Grant E, Hillyer EV, Bacharier L: "Natural history of asthma: persistence versus progression—does the beginning predict the end?" J Allergy Clin Immunol, 2008, pp. 607-613, vol. 121(3), doi: 10.1016/j.jaci.2008.01.006.
Prókai Á, Csohány R, Sziksz E, Pap D, Balicza-Himer L, Boros S, Magda B, Vannay Á, Kis-Petik K, Fekete A, Peti-Peterdi J, Szabó AJ: "Calcineurin-inhibition results in upregulation of local renin and subsequent vascular endothelial growth factor production in renal collecting ducts." Transplantation, 2015, pp. 325-333, vol. 100(2), doi: 10.1097/TP.0000000000000961.
Pujol-Autonell I, Ampudia RM, Monge P, Lucas AM, Carrascal J, Verdaguer J, Vives-Pi M: "Immunotherapy with Tolerogenic Dendritic Cells Alone or in Combination with Rapamycin Does Not Reverse Diabetes in NOD Mice." ISRN Endocrinol 2013, pp. 1-5, ID 346987, doi: 10.1155/2013/346987.
Rama I, Grinyó JM: "Malignancy after renal transplantation: the role of immunosuppression." Nat Rev Nephrol, 2010, pp. 511-519, vol. 6(9), doi: 10.1038/nrneph.2010.102.
Ryba M, Marek N, Hak Ł, Rybarczyk-Kapturska K, Mysliwiec M, Trzonkowski P, Mysliwska J: "Anti-TNF rescue CD4+Foxp3+ regulatory T cells in patients with type 1 diabetes from effects mediated by TNF." Cytokine, 2011, pp. 353-361, vol. 55(3), doi: 10.1016/j.cyto.2011.05.006.
Sénécal V, Deblois G, Beauseigle D, Schneider R, Brandenburg J, Newcombe J, Moore CS, Prat A, Antel J, Arbour N: "Production of IL-27 in multiple sclerosis lesions by astrocytes and myeloid cells: Modulation of local immune responses." GLIA, 2015, pp. 553-569, vol. 64(4), doi: 10.1002/glia.22948. 30.
Stelmaszczyk-Emmel A: (2015). "Regulatory T cells in children with allergy and asthma: it is time to act." Respir Physiol Neurobiol, 2015, pp. 59-63, vol. 209, doi: 10.1016/j.resp.2014.11.010.
Tang Q, Bluestone JA: "Regulatory T-cell therapy in transplantation-moving to the clinic." Cold Spring Harb Perspect Med., 2013, pii: a015552, vol. 3(11), doi: 10.1101/cshperspect.a015552.
Trzonkowski P, Bacchetta R, Battaglia M, Berglund D, Bohnenkamp HR, Ten Brinke A, Bushell A, Cools N, Geissler EK, Gregori S, Marieke Van Ham S, Hilkens C, Hutchinson JA, Lombardi G, Madrigal JA, Marek-Trzonkowska N, Martinez-Caceres EM, Roncarolo MG, Sanchez-Ramon S, Saudemont A, Sawitzki B: "Hurdles in therapy with regulatory T cells." Sci Transl Med, 2015, 7(304): 304ps18, doi: 10.1126/scitranslmed.aaa7721.
Trzonkowski P, Bieniaszewska M, Juscinska J, Dobyszuk A, Krzystyniak A, Marek N, Mysliwska J, Hellmann A: "First-in-man clinical results of the treatment of patients with graft versus host disease with human ex vivo expanded CD4+CD25+CD127-T regulatory cells." Clin Immunol, 2009, pp. 22-26, vol. 133(1), doi: 10.1016/j.clim.2009.06.001.

(56) References Cited

OTHER PUBLICATIONS

Trzonkowski P, Dukat-Mazurek A, Bieniaszewska M, Marek-Trzonkowska N, Dobyszuk A, Juscinska J, Dutka M, Mysliwska J, Hellmann A, (2013). "Treatment of graft-versus-host disease with naturally occurring T regulatory cells." Biodrugs, 2013, pp. 605-614, vol. 27(6), doi: 10.1007/s40259-013-0050-5.
Trzonkowski P, Szarynska M, Mysliwska J, Mysliwski A:, (2009). "Ex vivo expansion of CD4(+)CD25(+) T regulatory cells for immunosuppressive therapy." Cytometry A, 2009, pp. 175-188, vol. 75(3), doi: 10.1002/cyto.a.20659.
Vignali DA, Collison LW, Workman CJ:, (2008). "How regulatory T cells work." Nat Rev Immunol, 2008, pp. 523-532, vol. 8(7), doi: 10.1038/nri2343.
Wang YM, Zhang GY, Wang Y, Hu M, Wu H, Watson D, Hori S, Alexander IE, Harris DC, Alexander SI: "Foxp3-transduced polyclonal regulatory T cells protect against chronic renal injury from adriamycin." J Am Soc Nephrol, 2006, pp. 697-706, vol. 17(3), doi: 10.1681/ASN.2005090978.
Xiao F, Ma L, Zhao M, Huang G, Mirenda V, Dorling A, Lechler R, Lombardi G: "Ex vivo expanded human regulatory T cells delay islet allograft rejection via inhibiting islet-derived monocyte chemoattractant protein-1 production in CD34+ stem cells-reconstituted NOD-scid IL2rγnull mice." PLOS ONE, 2014, e90387, vol. 3;9(3), doi: 10.1371/journal.pone.0090387.
Yi S, Ji M, Wu J, Ma X, Phillips P, Hawthorne WJ, O'Connell PJ: "Adoptive transfer with in vitro expanded human regulatory T cells protects against porcine islet xenograft rejection via interleukin-10 in humanized mice." Diabetes, 2012, pp. 1180-1191, vol. 61(5), doi: 10.2337/db11-1306.
Zhang N, Su D, Qu S, Tse T, Bottino R, Balamurugan AN, Xu J, Bromberg JS, Dong HH: "Sirolimus is associated with reduced islet engraftment and impaired beta-cell function." Diabetes, 2006, pp. 2429-2436, vol. 55 (9), doi: 10.2337/db06-0173.
Zhao K, Ruan S, Yin L, Zhao D, Chen C, Pan B, Zeng L, Li Z, Xu K, (2015). "Dynamic regulation of effector IFN-γ-producing and IL-17-producing T cell subsets in the development of acute graft-versus-host disease." Mol Med Rep, 2015, pp. 1395-1403, vol. v13(2), doi: 10.3892/mmr.2015.4638.
Hans J. P. M. Koenen et al, "CD27/CFSE-Based Ex Vivo Selection of Highly Suppressive Alloantigen-Specific Human Regulatory T Cells", The Journal of Immunology, vol. 174, No. 12, Jun. 15, 2005 (Jun. 15, 2005), p. 7573-7583, XP055749735 DOI: 10.4049/jimmunol.174.12.7573 external link ISSN:0022-1767 1-11. p. 7575, left-hand column, paragraph 2; figures 1, 4.
Dorota Iwaszkiewicz-Grzes et al, "Antigen-reactive regulatory T cells can be expanded in vitro with monocytes and anti-CD28 and anti-CD154 antibodies", Cytotherapy, vol. 22, No. 11, Nov. 1, 2020 (Nov. 1, 2020), p. 629-641, XP055748287 DOI: 10.1016/j.jcyt.2020.07.001 external link ISSN:1465-3249.
International Publication (WO2021/034208) with International Search Report (PCT/PL2020/000073).
Office Action issued by the Japan Patent Office on May 28, 2024 for patent application No. JP2022-510078.
Anja Ten Brinke et al., "Monitoring T-Cell Responses in Translational Studies: Optimization of Dye-Based Proliferation Assay for Evaluation of Antigen-Specific Responses" Frontiers in Immunology , Dec. 2017 , vol. 8 , article No. 1870.
Dorota Iwaszkiewicz-Grzes et al., "Antigen-reactive regulatory T Cells can be expanded in vitro with monocytes and anti-CD28 and anti-CD154 antibodies" Cytotherapy , 2020 , vol. 22 , p. 629-641.

* cited by examiner

PROCESS FOR MANUFACTURING OF ANTIGEN-SPECIFIC T LYMPHOCYTES

The invention relates to the process for manufacturing of antigen-specific T lymphocytes (CellTrAg) for their clinical use in immunotherapy. CellTrAg produced in this way are suitable for treatment of autoimmune diseases, including e.g. multiple sclerosis, rheumatoid arthritis, type 1 diabetes mellitus, and for suppression of adverse immune responses, such as graft rejection, allergic reactions and graft versus host disease GVHD.

Treg lymphocytes constitute for about 1% of all peripheral blood lymphocytes, but are important for maintaining the tolerance of their own tissues (Trzonkowski P 2009) (Vignali D A 2008) (Yi S 2012). Lack of regulatory T cells leads to a number of autoimmune diseases and hypersensitivity, as seen in the case of patients with X-linked immunodeficiency syndrome, polyendocrinopathy and enteropathy (IPEX) (Gambineri E 2003). Treg lymphocytes can be called "intelligent steroids" because as steroids, they inhibit inflammatory reactions and act immunosuppressively, but in contrast the physiological suppressor effect of Treg cells concerns only pathological reactions (eg. directed against its own tissues). The results of clinical trials, including our observations, indicate that therapy with Treg lymphocytes is safe and does not impair the immune response against foreign and dangerous antigens (viruses, bacteria, cancer cells) (Marek-Trzonkowska N 2012) (Marek-Trzonkowska N 2014) (Martelli M F 2014) (Bluestone J A 2015).

Our research team has been conducting research on the biology and clinical use of Treg lymphocytes for over 10 years. We were the first who used in vitro amplified Treg cells in the treatment of graft-versus-host disease (GvHD) in adults (NKEBN/458-310/2008) (Trzonkowski P 2009), and then in type 1 diabetes (T1D) in children (TregVAC ISRCTN06128462; TregVAC2.0EudraCT:2014-004319-35) (Marek-Trzonkowska N 2012) (Marek-Trzonkowska N 2014) and in multiple sclerosis (TregSM EudraCT:2014-004320-22) (Trzonkowski P 2015). Currently, clinical trials using Treg cells are also conducted by other centers in the world and relate to therapy/prevention of GVHD (Di lanni M 2011), T1D treatment in adults (NCT01210664), as well as induction of tolerance in kidney transplantation (i.a. NCT02091232 and NCT02129881) and liver (ThRIL NCT02166177 and NCT01624077). In recent years, the dynamic development of cellular therapies using Treg lymphocytes as a therapeutic tool has begun. Currently, about 40 clinical trials are conducted with these cells in the world. All of these projects are guided by one goal, namely intelligent immunosuppression, which would inhibit unwanted immune reactions without impairment the physiological immune response (Trzonkowski P 2015, Gliwinski M 2017).

During above studies, Treg lymphocytes were obtained from the peripheral blood of patients or from umbilical cord blood units. The best method of isolation is to use a sorter, which results in a very pure (97-100%) population of these cells. Typically, lymphocytes with the CD3+CD4+CD25high phenotype or CD3+CD4+CD25highCD127- or CD3+CD4+CD25highCD127low are isolated (Application P. 399447) (Trzonkowski P 2009) (Marek-Trzonkowska N 2012) (Marek-Trzonkowska N 2014) (Trzonkowska P 2015). The isolated cells are then activated for intense proliferation for 10-14 days to obtain an amount sufficient to be administered to the patient. Effective expansion must be carried out under conditions while maintaining the full phenotype, including in particular high expression of FoxP3 factor, which is determined by specific laboratory activities (Marek N 2011, Golab K 2013, Marek-Trzonkowska N 2017). In addition, expansion in such a scheme for clinical applications must be carried out in accordance with the standards of Good Manufacturing Practice (GMP) because the Treg lymphocyte preparation is classified as an Advanced Therapy Medicinal Product (ATMP) and is subject to Pharmaceutical Law and Regulation No 1394/2007 of the European Parliament "on advanced therapy medicinal products".

The use of cells produced according to the above scheme implies their polyspecificity—it is a set of lymphocytes with specificity against many different antigens, and thus their effectiveness after administration is limited. Of course, the fact that all Treg lymphocytes have tropism to the sites of inflammation, the ability to regulate the 'bystander' type and the ability to convert other cells to the regulatory phenotype on the basis of infective tolerance affect the high efficiency of polyspecific (polyclonal) products. Nevertheless, the effectiveness of such a product can be increased by targeting cells to specific antigens. In this way, such antigen-specific Tregs lymphocytes could only migrate to sites where the expression of such antigens occurs and selectively inhibit the activity of pathological effector cells that recognize such antigens only at the site of inflammatory response induced by stimulation of such antigen. In the case of autoimmune diseases, it would be possible to suppress the destruction of affected organs (eg insulin-producing pancreatic islets in type 1 diabetes or myelin sheaths in multiple sclerosis). At the same time, it would limit the systemic side effects of Tregs lymphocytes, which instead of circling the entire lymphatic system would only show tropism to sites expressing the specific antigen to which they are sensitized.

The development of a safe, simple to use and simultaneously economically viable method of multiplying stable Treg lymphocytes with specific antigenic specificity and high suppressor potential is of key importance for the development and success of clinical trials using Treg cells as a therapeutic tool.

Seemingly another issue is an excessive immune response, also known as hypersensitivity to allergens. Most of these disorders are successfully treated symptomatically using available drugs. However, some forms of hypersensitivity can lead to severe disability and even complications leading to death. The disease process often progresses over time, inflammation intensifies, leading to permanent structural changes in the airways, and the drugs used cease to be effective (Panettieri R A Jr 2008) (Barbaro M P 2014). In this situation, also antigen-specific Treg lymphocytes could become a modem antiallergic drug.

In conclusion, effective and safe drugs used both in the treatment of autoimmune diseases, allergies and transplant recipients are those that maximally selectively regulate the immune system response to well-defined antigens responsible for unwanted immune response (eg, an autoimmune disease or allergy, rejection organ, graft-versus-host disease) and at the same time do not impair the physiological immune response to foreign and dangerous antigens. The chance for such intelligent immunosuppression are precisely the antigen-specific Treg lymphocytes. The condition for the success of clinical therapy with Treg cells, however, is the development of a patient-safe protocol for the expansion of these lymphocytes, which would guarantee a high number of antigen-specific cells while maintaining their stability and suppressor activity throughout the duration of the culture (Tang Q 2013). The method described in this patent application meets the requirements described above.

In particular, the present invention provides process for manufacturing of antigen-specific T lymphocytes marked with monoclonal antibodies and sorted wherein the lymphocytes:

a) are generated by the use of autologous monocytes loaded with the antigen;
b) T regulatory or T effector lymphocytes to be generated are suspended in PB S and stained intracellularly with a fluorescent dye;
c) the lymphocytes are subsequently incubated in the dark;
d) the lymphocyte cells are subsequently washed intensively several times with culture medium;
e) T regulatory or T effector lymphocytes stained with intracellular fluorescent dye are suspended in the culture medium with gamma-irradiated autologous CD14+ monocytes loaded with antigen;
f) the co-culture of T regulatory or T effector lymphocytes with CD14+ monocytes is coincubated with anti-CD154 and anti-CD28 antibodies;
g) the co-culture is incubated in culture medium; and
h) antigen-specific T lymphocytes after incubation are sorted based on the low intensity of intracellular dye where the low intensity of fluorescence is a marker of antigen-specificity in that a loss of fluorescence correlated with the intensity of proliferation.

In the process as defined above, it is preferred that the T regulatory or T effector lymphocytes are suspended in the following concentration: $1\times10^6$ cells/ml PBS.

In the process as defined above, it is preferred that the lymphocytes are stained with one of the following fluorescent dyes: CFSE or Violet Blue in the final concentration 1-5 μM.

In the process as defined above, it is preferred that the lymphocytes are incubated 20 minutes at room temperature or at 37° C.

In the process as defined above, it is preferred that autologous monocytes are added to the co-culture in the final monocyte:lymphocyte ratio of 1:1.

In the process as defined above, it is preferred that the monocytes are gamma-irradiated.

In the process as defined above, it is preferred that the co-culture of monocytes and lymphocytes is incubated with anti-CD154 antibodies in the final concentration of 5 μg/ml and anti-CD28 antibodies in the final concentration of 5 μg/ml.

In the process as defined above, it is preferred that the co-culture is incubated at 37° C. in 5% $CO_2$.

In the process as defined above, it is preferred that the specificity to antigen is assessed in functional tests in which antigen-specific T lymphocytes, in particular the T lymphocytes sorted based on low fluorescence of the intracellular dye, are more active than unspecific T lymphocytes, in particular the T lymphocytes sorted based on preserved high fluorescence of the intracellular dye where the activity in the case of T regulatory lymphocytes is defined as the suppression of function T effector lymphocytes, while in the case of T effector lymphocytes the activity is defined as increased intensity of proliferation and increased intensity of production of cytokines and cytotoxic factors.

The present invention are illustrated by the following examples, which are not its limitation.

MATERIALS AND METHODS

Figure 1:
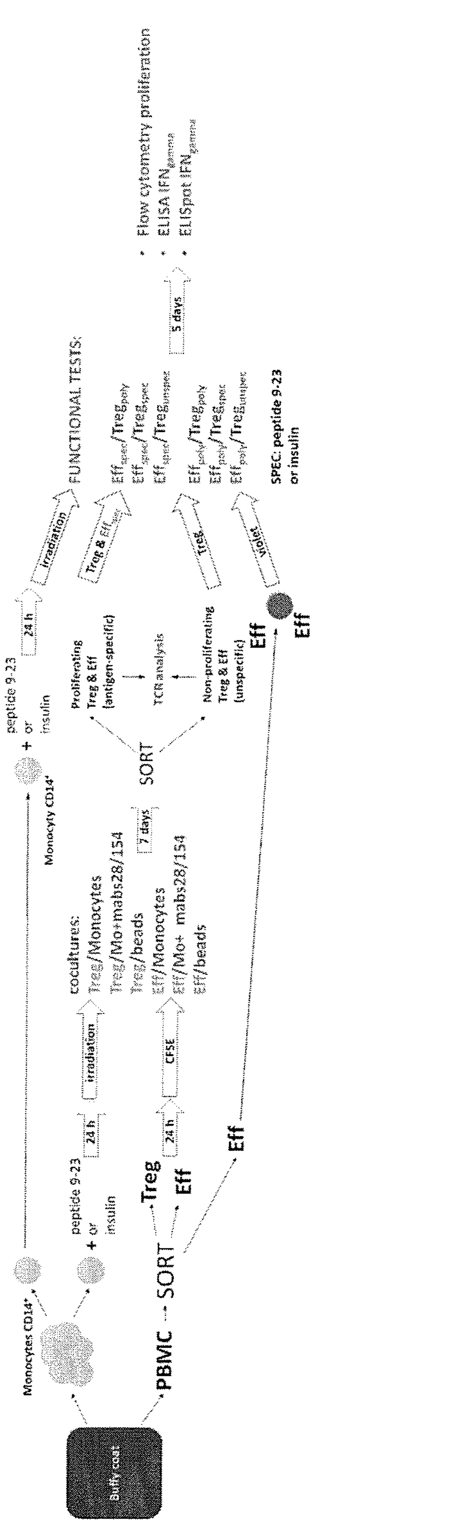
FIG. 1—presents scheme of the experiments. Buffy coat was separated to monocytes and lymphocytes. Lymphocytes were sorted into T regulatory cells (Treg) and T effector cells (Eff), stained with CFSE and stimulated with irradiated monocytes preloaded with peptide (insulin or peptide 9-23). Polyclonal Tregs and Eff were generated with antiCD3/antiCD28 beads. After 7 days of the coculture, the cells were sorted according to diluted fluorescence of CFSE using the protocol showed in FIGS. 2C and 2D into antigen-specific and unspecific cells. The obtained polyclonal ($Treg_{poly}$), antigen-specific ($Treg_{spec}$) and unspecific ($Treg_{unspec}$) subsets of Tregs were then tested in functional tests in which the responders were violet-stained autologous T cell effectors, either polyclonal ($Eff_{poly}$) or antigen-specific ($Eff_{spec}$). $Eff_{spec}$ were prepared using stimulation with irradiated monocytes preloaded with the antigen.

Overview of the method and functional analysis is presented on FIG. 1.

Blood Donors

Buffy coats were obtained from the Regional Centre for Blood Donation and Treatment in Gdańsk.

B:9-23 Insulin Peptide and Insulin

B:9-23 insulin peptide was synthesized at Lipopharm (Gdansk, Poland) as white powder with purity >90% using HPLC method. Peptide was dissolved in deionized, autoclaved water for a final concentration of 0.5 μg/μ1 and stored in −70° C. for no longer than 3 months.

Insulin used in tests were commercially available (Actrapid® Penfill®, Novo Nordisk A/S) and was stored in the fridge in 2-8° C.

Cell Isolation and Sorting

T Regulatory Cells and T Effector Cells

Figure 2:
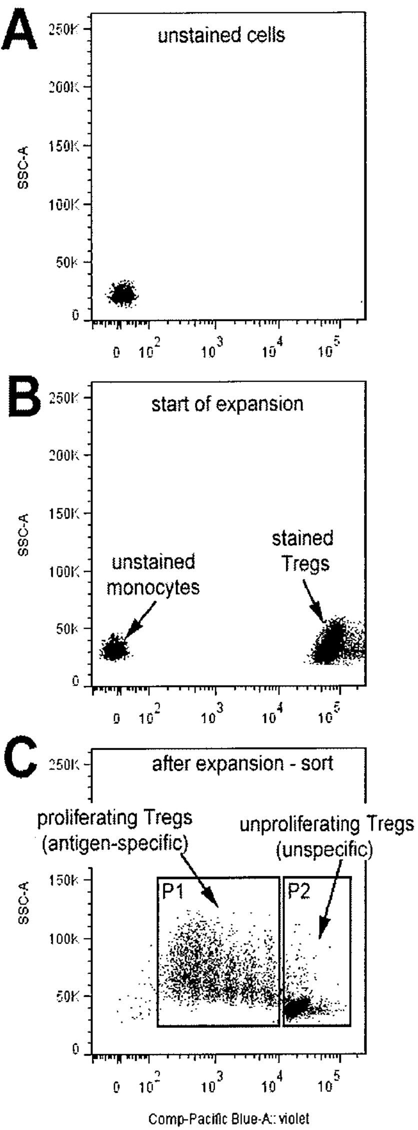
FIG. 2—presents antigen-specific regulatory T cell sorting method. To distinguish Tregs from other cells (A), in particular from antigen presenting monocytes used during stimulation, they are stained with a fluorescent dye (B). After finishing of the co-culture, Tregs lymphocytes that recognized the antigen arrange in the field of reduced fluorescence (P1 gate) were sorted as a separate antigen-specific population.

Overview of the preparation of cells and sorting is presented on FIG. 2. Peripheral blood mononuclear cells (PBMCs) were isolated from buffy coats obtained from healthy volunteer blood donor by Ficoll-Hypaque gradient centrifugation and were used fresh. Tregs and Teffs were freshly isolated according to our previously described protocol. Briefly, $CD4^+$ T cells were separated by negative selection using EasySep Human CD4+ T Cell Enrichment Kit (Stemcell Technologies) according to manufacturer's instructions. Subsequently, $CD4^+$ T cells were stained with monoclonal antibodies (mAb) specific for the following antigens: CD3, CD4, CD25 and CD127. Then, cells were sorted with FACS AriaIIu sorter (BD Biosciences, USA) into the following phenotype of Tregs: $CD3^+CD4^+CD25^{High}CD127^{-/Low}lin^-doublet^-$ and Teffs: $CD3^+CD4^+CD25^-CD127^{High}lin^-doublet^-$. Isolated Treg lymphocytes and Teff cells were cultured on separate plates and incubated at 37° C. in culture medium X-VIVO20 (Lonza) which meets the GMP standards. The medium was supplemented with heat inactivated human AB serum (10%), interleukin 2 (IL-2; 2000 U/ml; Proleukin; Chiron, San Diego, CA), penicillin (100 U/ml) and streptomycin (100 mg/ml) for 24 h.

Monocytes

Autologous CD14+ cells were separated by positive selection using EasySep™ Human CD14 Positive Selection Kit II (StemCell Technologies) according to manufacturer's instructions with the purity above 95%. Isolated monocytes were then cultured ($10^6$ cells/well) and incubated at 37° C. in culture medium X-VIVO20 (Lonza) which meets the GMP standards. A previously prepared peptide solution (25 μg/well/ml) or insulin (100 W/well/nil) was added for 24 h. We prepared three conditions: monocytes stimulated with B:9-23 insulin peptide ($Mo_{9-23}$), insulin ($Mo_{INS}$) or without stimulation (Mo).

Dye-Labeling and Cell Expansion

Monocytes

After 24 h incubation, the monocytes were collected from the wells and irradiated with gamma irradiation (in standard conditions as for irradiation of blood preparations), counted and resuspended in fresh medium (X-VIVO20) at a final concentration of $1\times10^6$ cells/ml.

Treg Cells and Teff Cells 24 h after sort, T regulatory lymphocytes were collected from the wells, washed with PBS to remove serum that affects staining. Then cells were resuspended in PBS at a concentration of $1\times10^6$ cells/ml and stained with CFSE (Cell Trace CFSE Cell Proliferation Kit, Life Technologies) at final CFSE concentration between 1 and 5 μM. The cells were incubated 20 minutes at 37° C. in the dark and intensively washed several times with PBS and then with culture medium (X-VIVO20+10% serum+penicillin/streptomycin). T effector cells were also stained in a similar manner.

Alternatively, both lymphocyte populations were stained with violet (Cell Trace Violet Cell Proliferation Kit, Life Technologies) in the above manner at a final concentration between 1 and 5 μM.

The staining control was performed on flow cytometer (Fortessa, BDBioscience).

Polyclonal Stimulation

After staining step, part of cells were suspended with fresh medium (X-VIVO20, Lonza) containing 10% inactive human serum and antibiotics penicillin/streptomycin (Sigma Aldrich). Next, cells were seeded on 96-well plates ($1\times10^5$ cells/well) and stimulated with magnetic beads coated with anti-CD3 and anti-CD28 antibodies (Treg Expansion Kit, Miltenyi Biotech) in 1:1 ratio (bead:cell) and cultured for 7 days. We prepared two conditions of polyclonal cells—$Treg_{POLY}$ and $Teff_{POLY}$.

Antigen Stimulation

After staining step, part of cells were suspended with fresh medium (X-VIVO20, Lonza) containing 10% inactive human serum and antibiotics penicillin/streptomycin (Sigma Aldrich). Next, cells were seeded on 96-well plates ($1\times10^5$ cells/well) and stimulated with monocytes loaded with antigen: B:9-23 insulin peptide ($Mo_{9-23}$) or insulin ($Mo_{INS}$) in 1:1 ratio (Mo:cell). Subsequently, sterile anti-CD154 (Purified NA/LE Mouse Anti-Human CD154; BD Biosciences) and anti-CD28 (Purified NA/LE Mouse Anti-Human CD28; BD Biosciences) to final concentrations of 5 μg/ml were added to the co-culture. Prepared co-culture was incubated at 37° C. in 5% $CO_2$ in culture medium (X-VIVO20+10% serum+penicillin/streptomycin. We prepared two conditions of cells—$Treg_{9-23/INS+CD28CD154}$ and $Teff_{9-23/INS+CD28CD154}$. At the same time we prepared cells stimulated with monocytes loaded with antigens but without anti-CD28 and anti-CD154-$Treg_{9-23/INS}$ and $Teff_{9-23/INS}$. As a negative control we used cells without monocytes (not stimulated, non-proliferating). As a positive control we used polyclonal cells (index POLY). Cells were culture for 7 days.

Sorting of Antigen-Specific Cells

At day 7 of the expansion cells were collected and washed with fresh medium (X-VIVO). Cells were sorted with FACS AriaIIu sorter (BD Biosciences, USA) from the SSC-A dot plot (side scatter) versus 488 nm channel for Cell Trace CFSE Cell Proliferation Kit (Life Technologies) or SSC-A versus 450 nm channel for Cell Trace Violet Cell Proliferation Kit (Life Technologies). Proliferating cells (index PRO), in response to antigen presented by monocytes, were identified as those that showed a fluorescence lower than the cells from the negative control [cutoff for the sorting gate assumed for fluorescence intensity below the negative control peak, goal containing no more than 5% peak events negative control with the lowest fluorescence]. Non-proliferating cells (index NON) as those whose fluorescence was comparable to cellular fluorescence from the negative control [sorting gates assumed for fluorescence intensity of the negative control peak, goal containing not less than 80% of events of the negative control peak]. Obtained cells were subjected to quality control (phenotype control, functional test to inhibit proliferation and production of interferon γ) or further cultured with the addition of magnetic microspheres coated with anti-CD3 and anti-CD28 (Miltenyi Biotec) antibodies in a 1:1 ratio (cell:bead) to obtain as many antigen-specific T regulatory lymphocytes as possible.

Quality Control

Phenotype Check

At 7th day of the expansion samples of Tregs and Teffs were labeled with Abs against the following antigens (Ag): CD4, CD25, CD127, CD45RA (BD Biosciences, USA), CD62L (Life Technologies, USA), FoxP3 using Foxp3 Staining Buffer Set (eBioscience, USA) and analyzed with flow cytometry (Fortessa, BD Biosciences, USA).

Proliferation Inhibition Assay

At $7^{th}$ day of expansion we performed functional assay of inhibition of interferon-γ (IFN-γ) production. Treg and Teff cells were washed with PBS buffer, purified from microspheres used for stimulation by magnet and counted. The cells were then resuspended in fresh culture medium containing antibiotics and human heat inactivated human AB serum (10%). Over the next two days, cells from individual conditions were still cultured separately. IL-2 and activating microspheres were not added during this time. After 48 h, Teff cells were washed with PBS buffer and counted. Teff cells were stained with CFSE (Cell Trace CFSE Cell Proliferation Kit, Life Technologies, 1 μM, 15 min, 37° C.) or violet (Cell Trace Violet Cell Proliferation Kit, Life Technologies, 1 μM; 15 min, 37° C.) to analyze their proliferation in the presence of Treg lymphocytes. The dye selection was determined by the previous Treg lymphocytes staining—if Tregs were stained with CFSE, Teff cells were stained with violet and vice versa.

Marked autologous Teff cells (responders) were mixed in the following proportions with Treg cells (specific, non-specific and polyclonal): 1:1, 1:½, 1:¼ and 1:⅛. The number of Teff cells was constant each time and the number of Treg lymphocytes was variable. Cells were suspended in fresh culture medium containing heat inactivated human AB serum (10%), interleukin 2 (IL-2; 100 U/ml) and antibiotics: penicillin (100 Um') and streptomycin (100 mg/ml). As stimulants we used irradiated autologous monocytes loaded with antigen ($Mo_{9-23}$ or Mows) which were added in 1:1 ratio with Teff. As a positive control we used Teff (without Treg cells) stimulated with monocytes ($Mo_{9-23}$ or Mows) or microspheres coated with anti-CD3 and anti-CD28 antibodies. As a negative control we used Teff cells without stimulation (reference to read in cytometer). Additional control were unstained Treg cells that were cultured without Teff cells.

Cells were cultured for 6 days at 37° C. in 5% $CO_2$ in culture medium (X-VIVO20+10% serum+p/s). After this time, cells were harvested and analyzed using a flow cytometer (Fortessa, BD Biosciences). Unstimulated Teff cells cultured without Treg cells were used as a background and was used as a 100%, what means that 100% of cells didn't divide. Stimulated Teff cells cultured without Treg cells were used as 0%, what means that proliferation wasn't inhibit.

Inhibition of INF-γ Production by Teff Cells Cultured with Treg Cells

A sample of Treg lymphocytes from each cultured condition was collected for functional tests to confirm the inhibitory effect of Treg cells on IFN-γ secretion by autologous Teff cells. In parallel, sample of Teff lymphocytes was collected, which were previously expanded under the same conditions like tested Treg, as responders in the proliferation inhibition assay. In this way, two series of tests could be carried out as responders: polyclonal Teff ($Teff_{POLY}$) and antigen specific (proliferating) Teff ($Teff_{9-23-PRO}$ or $Teff_{INS-PRO}$)

Cells intended to test (Tregs and Teffs) were washed with PBS, purified from microspheres used for stimulation and counted. Next, cells were suspended in fresh medium containing heat inactivated human AB serum (10%) and antibiotics (penicillin/streptomycin. Over the next two days, cells from individual conditions were still cultured separately. IL-2 and activating microspheres were not added during this time.

Marked autologous Teff cells (responders) were mixed in the following proportions with Treg cells: 1:1, 1:½, 1:¼ and 1:1/8. The number of Teff cells was constant each time and the number of Treg lymphocytes was variable. Cells were suspended in fresh culture medium containing heat inactivated human AB serum (10%), interleukin 2 (IL-2; 100 U/ml) and antibiotics: penicillin (100 U/ml) and streptomycin (100 mg/ml). As stimulants we used irradiated autologous monocytes loaded with antigen ($Mo_{9-23}$ or $Mo_{INS}$) which were added in 1:1 ratio with Teff. As a positive control we used Teff (without Treg cells) stimulated with monocytes ($Mo_{9-23}$ or $Mo_{INS}$) or microspheres coated with anti-CD3 and anti-CD28 antibodies. As a negative control we used Teff cells without stimulation (reference to read in cytometer). Additional control were unstained Treg cells that were cultured without Teff cells.

Cells were cultured for 6 days at 37° C. in 5% $CO_2$ in culture medium (X-VIVO20+10% serum+p/s). After this time, supernatants were harvested from under culture and IFN-γ levels were determined by ELISA according to the manufacturer's instructions (Human IFN-gamma OptEIA Kit II, BD Biosciences).

INF-γ—ELISpot

Co-cultures of Teff lymphocytes (responders) with Treg lymphocytes were breeded for 48 h on special ELISpot plates. This method allows to identify exactly how many cells produced the cytokine (INF-γ). After incubation, the plates were washed from the cells and plates were stained according to the manufacturer's instructions (MABtech). The readings were made in the ELISPOT plate reader (Immunospot 5, CTL).

RESULTS

Effectiveness of Obtaining Antigen-Specific T Regulatory Cells Stimulated with Monocytes Displaying Antigen and Anti-CD28 and Anti-CD154 Antibodies Analysis of the percentage of Tregs generated by autologous antigen presenting monocytes, i.e. antigen-specific regulatory T cells, showed that proliferation of these cells is higher when anti-CD28 and anti-CD154 antibodies were added to the co-culture, especially for co-cultures with insulin (t-test difference without antibodies/with the addition of antibodies: insulin p=0.041, peptide 9-23 p=0.044). (FIG. 3A)

Comparing the effect of peptides used on Tregs proliferation generated by autologous antigen presenting monocytes, we have shown that the presented peptide 9-23 significantly more strongly increased compared to insulin the percentage of these cells in cultures without anti-CD28 and antiCD154 antibodies (t-test p=0.032). The use of anti-CD28 and antiCD154 antibodies in the coculture resulted in the percentage of proliferating Treg lymphocytes being similar in both cohorts (t-test p=0.54).

Figure 3:
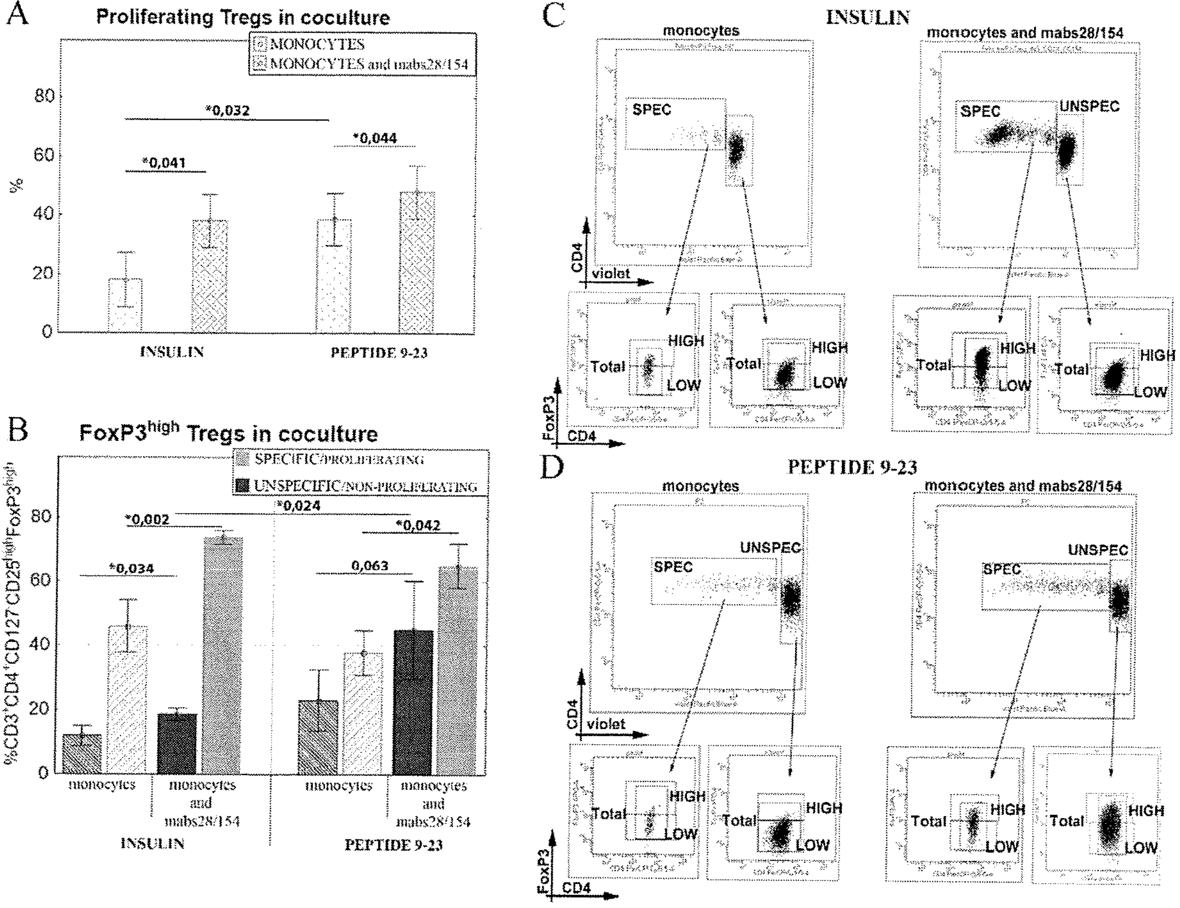
FIG. 3—presents percentage of Tregs responding to the antigens in cocultures with monocytes. The analysis covered Treg cells cocultured with monocytes presenting the antigens: insulin or peptide 9-23. In some cultures monoclonal antibodies anti-CD28 and antiCD154 (mabs28/154) were added to provide the second signal. The percentage of proliferating (antigen-specific) Tregs (A) and the percentage of Tregs expressing high intensity of FoxP3 expression (high) and either proliferating (light blue) or not proliferating (dark blue) (B) was assessed. The results are presented as mean+/−SD. The examples of the analysis are shown in the dot-plots in chart C from cocultures stimulated with monocytes loaded with insulin and chart D from cocultures stimulated with monocytes loaded with peptide 9-23. Gates in the dot-plots CD4 vs. Violet show on the left proliferating (SPEC) antigen-specific Tregs and on the right non-proliferating (UNSPEC) unspecific Tregs. Arrows link corresponding dot-plots showing the expression of FoxP3. Upper gates represent $FoxP3^{high}$ and lower $FoxP3^{low}$ subsets of the cells.

Examples of dot-plots and the method of analysis are presented on FIG. 3C,3D.

Expression of the FoxP3 Transcription Factor by Antigen-Specific T Regulatory Lymphocytes Stimulated with Monocytes Presenting Antigen and Anti-CD28 and Anti-CD154 Antibodies In all cultures throughout the entire experiment, the percentage of lymphocytes expressing FoxP3 did not fall below 90%.

The percentage of Treg cells showing high expression of the FoxP3 transcription factor (i.e. the CD3+CD4+CD25highCD127-FoxP3high phenotype) stimulated by autologous antigen presenting monocytes was significantly higher for antigen specific/proliferative populations compared to the corresponding non-specific/non-proliferating Treg lymphocytes (all t-tests p<0.05) (FIGS. 3B-D).

The percentage of Treg cells showing high expression of FoxP3 transcription factor was significantly increased when anti-CD28 and antiCD154 antibodies were added to the co-culture for both antigen-specific/proliferating Treg cells (t-test difference with/without antibodies: insulin p=0.002, peptide 9-23 p=0.042) as in the case of non-specific/non-proliferating Treg lymphocytes (t-tests difference without/with antibodies: insulin p=0.034 and only trend for peptide 9-23 p=0.063).

Clonality Analysis Based on the Repertoire of TCRs of Tregs Lymphocytes

Figure 4:
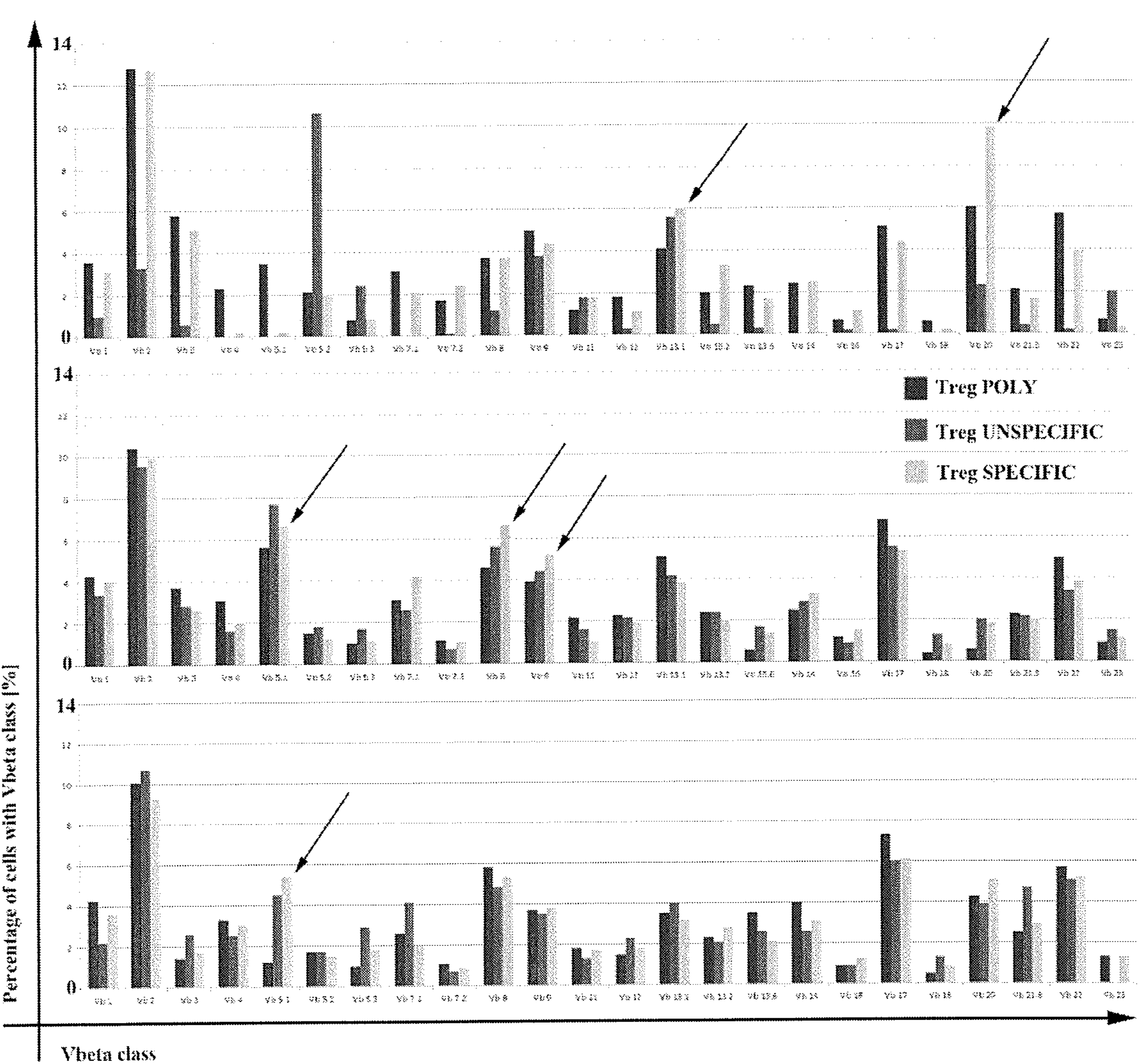
FIG. 4—presents Treg lymphocytes clonality. Treg lymphocytes clonality measured by expression of individual classes of TCR receptors (Vβ chains). Examples of Treg lymphocytes clonal analyses before culture (‘Treg POLY’) and after co-culture with monocytes presenting antigen (insulin or 9-23 peptide) sorted based on proliferative ability: proliferating cells (‘Treg SPECIFIC’) and non-proliferative cells (‘Treg UNSPECIFIC’). On the arrows, clones identified as preferentially stimulated to proliferate during co-culture (the percentage visibly increased after the co-culture relative to ‘Treg POLY’). In each of the cultures carried out, there were clones with a different Vβ expression, in each culture no more than one or two clones increased preferentially, and the growth did not exceed a few percent.

Analysis of changes in clonality of TCR receptoire in the antigen-specific/proliferating Treg lymphocytes population showed that in each culture the percentage of one-two clones, each time with a different TCRbeta specificity, increased. Nevertheless, these increases are not greater than a few-dozen percent of all proliferating cells (FIG. 4).

Functional Test—Inhibition of T Effector Lymphocytes Proliferation

Figure 5:
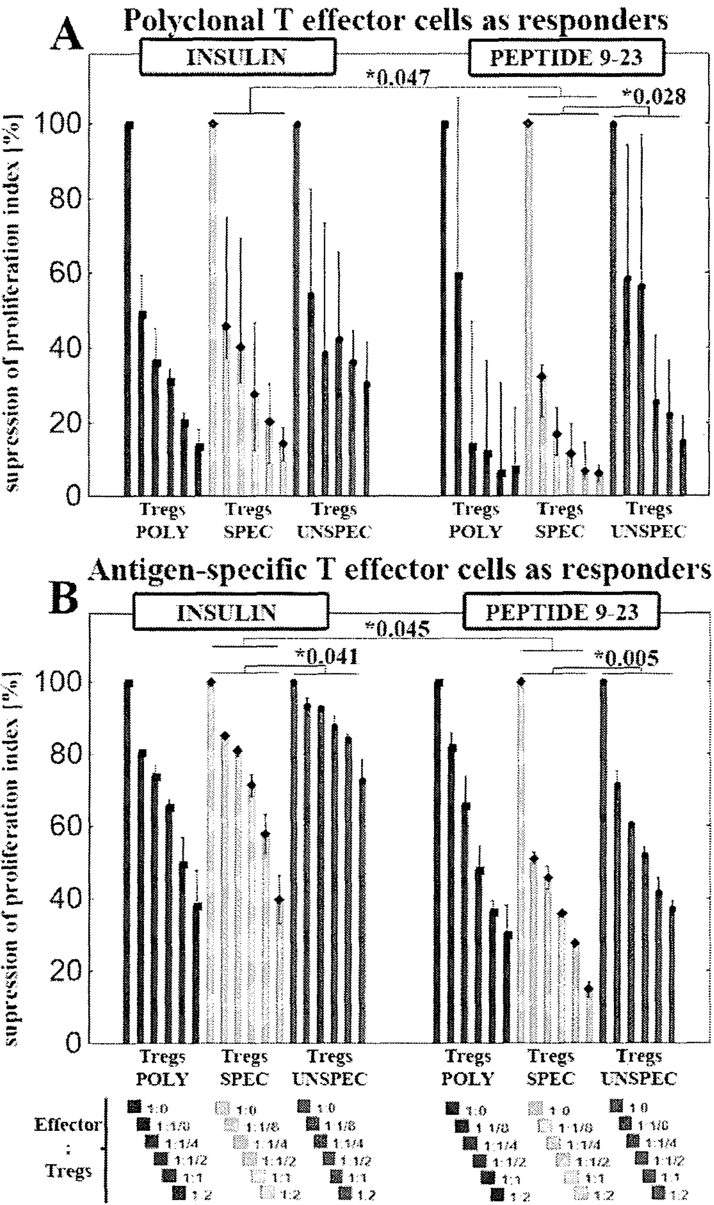
FIG. 5—presents Functional test—Inhibition of T effector lymphocytes proliferation. The generated subsets of Tregs (Tregs), such as polyclonal (Tregs POLY), antigen-specific towards insulin or peptide 9-23 (Tregs SPEC) and unspecific (Treg UNSPEC) cells were cocutured with autologous T effector cells (Effector) in the proportions given at the bottom of the figure. Effectors were treated as responders, either polyclonal (A upper chart) or antigen-specific (B lower chart). The cocultures were then stimulated with irradiated monocytes preloaded with insulin or peptide 9-23. The readout was the suppression of proliferation of the responders. The results are indexed to the cultures of responders only which proliferation was always taken as 100%. Results are shown as means+/−min.-max. Significant differences are marked with /* and p value.

Analysis of the immune response in proliferation suppression assays confirmed the suppressive effects of all investigated Treg lymphocytes subpopulations (ANOVA, p<0.05) (FIG. 5).

Efficacy of Peptides

Comparative analysis showed statistically significant higher specific Tregs performance for peptide 9-23 compared to specific Tregs for insulin for tests when the inhibited responders in the experiment were polyclonal effector T cells (ANOVA, F=8.03 p=0.047) (FIG. 5A) and effector T cells specific for tested antigen (ANOVA, F=20.40 p=0.045) (FIG. 5B).

Polyclonal Versus Specific

The effectiveness of the proliferation inhibition was higher in the tests with specific Tregs compared to the polyclonal Tregs but did not reach statistical significance in any of the tests (ANOVA, p<0.05).

Nevertheless, it has been shown that specific Tregs component is mainly responsible for the suppressive effect in the tests. After separating specific Tregs (proliferating) from nonspecific Tregs (non-proliferating), specific Tregs inhibited significantly more T effector cells response compared to non-specific Tregs. This significance concerned both tests in which the responders were polyclonal effector T cells (significant only for peptide 9-23: ANOVA, F=8.21 p=0.028, for insulin: ANOVA, F=1.31 p=0.33), as well as specific T effector lymphocytes (for peptide 9-23: ANOVA, F=186.32 p=0.005, for insulin: ANOVA, F=22.47 p=0.041).

Functional Test—Inhibition of Interferon Secretion

Figure 6:
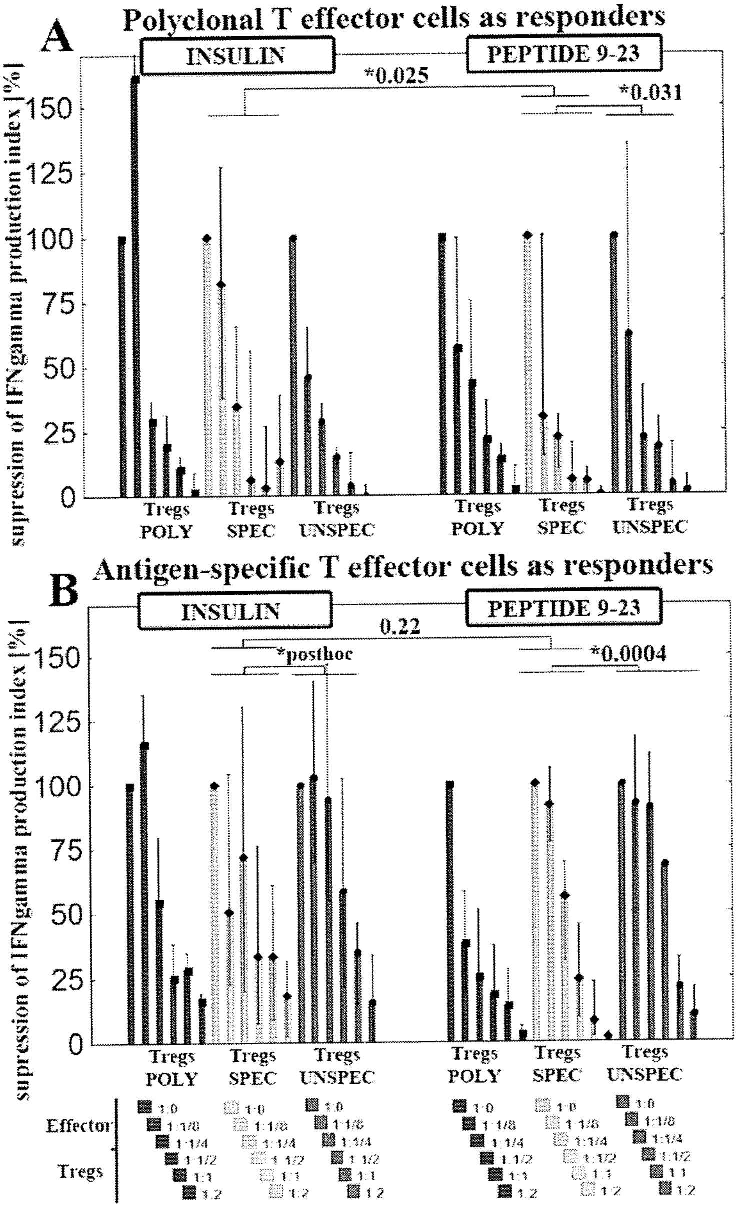
FIG. 6—presents Functional test—Inhibition of IFN-gamma production by T effector lymphocytes (ELISA). The generated subsets of Tregs (Tregs), such as polyclonal (Tregs POLY), antigen-specific towards insulin or peptide 9-23 (Tregs SPEC) and unspecific (Treg UNSPEC) cells were cocutured with autologous T effector cells (Effector) in the proportions given at the bottom of the figure. Effectors were treated as responders, either polyclonal (A upper chart) or antigen-specific (B lower chart). The cocultures were then stimulated with irradiated monocytes preloaded with insulin or peptide 9-23. The readout was the suppression of IFN-gamma production by the responders. The results are indexed to the cultures of responders only which proliferation was always taken as 100%. Results are shown as means+/−min.-max. Significant differences are marked with /* and p value.
Figure 7:
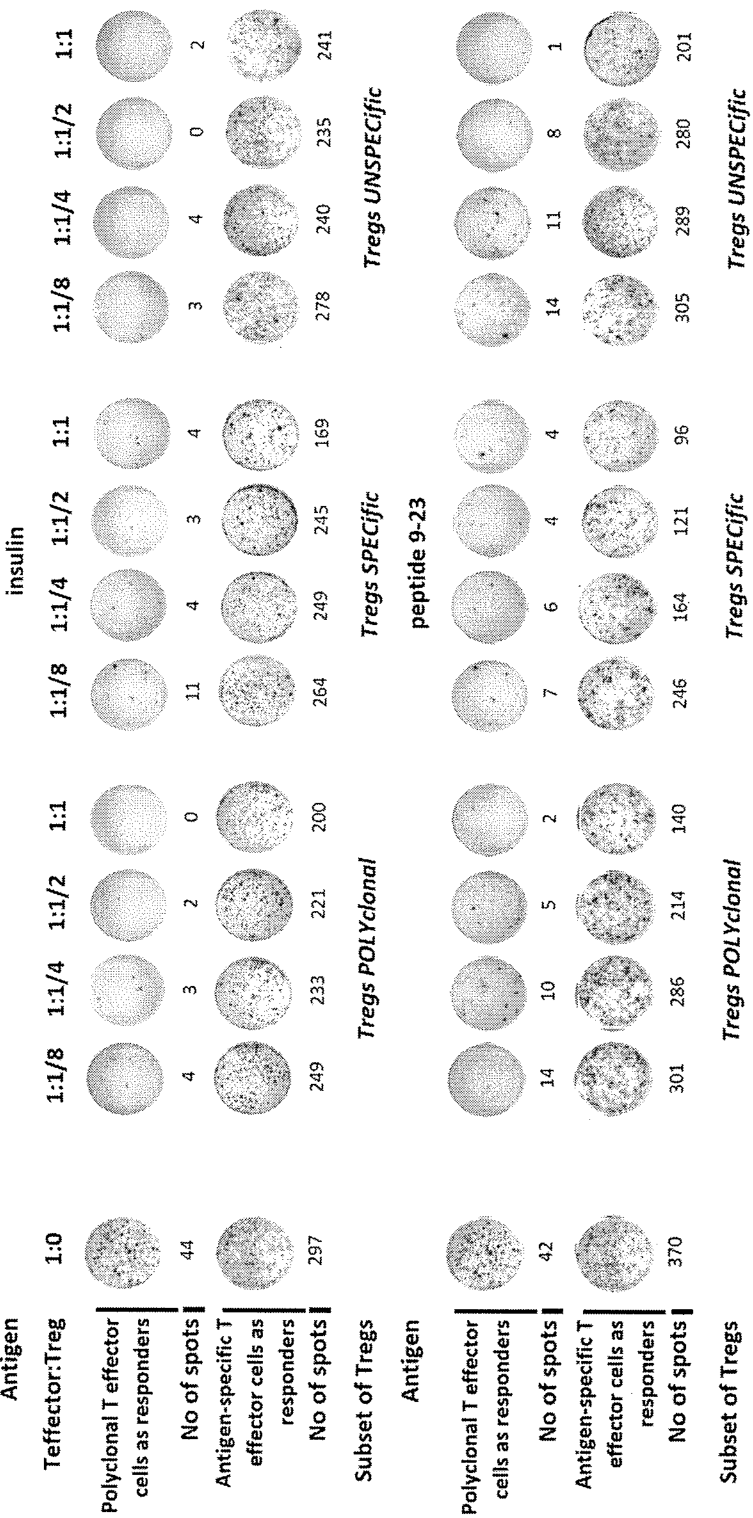
FIG. 7—presents Functional test—Inhibition of IFN-gamma production by T effector lymphocytes—ELISPOT. The generated subsets of Tregs (Tregs), such as polyclonal (Tregs POLYclonal), antigen-specific towards insulin or peptide 9-23 (Tregs SPECific) and unspecific (Treg UNSPECific) cells were cocutured with autologous T effector cells as responders, either polyclonal or antigen-specific. Tregs with effectors were cocultured in the proportions given at the top of the figure. The cocultures were then stimulated with irradiated monocytes preloaded with insulin or peptide 9-23. The readout was the suppression of IFNgamma production by the responders. The results are shown as the pictures of the cultures and number of spots in particular wells.

Analysis of the immune response in interferon gamma suppression inhibition assays confirmed the suppressive action of all investigated Tregs lymphocyte subpopulations (ANOVA, p<0.05) (FIGS. 6 and 7).

Efficacy of Peptides

Comparative analysis showed a higher for 9-23 peptide specific Tregs performance compared to full insulin specific Tregs when the responders inhibited in the experiment were polyclonal T effector cells (ANOVA, F=5.78 p=0.025) (FIGS. 6A and 7). A similar difference was observed when the responders inhibited in the experiment were specific T effector cells for tested antigen, however the difference did not reach statistical significance (ANOVA, F=1.86 p=0.22) (FIGS. 6B and 7).

Polyclonal Versus Specific

The response inhibition efficiency was higher in tests with specific Tregs compared to the polyclonal ones but did not reach statistical significance in any of the tests (ANOVA, p<0.05).

Nevertheless, in the case of peptide 9-23 stimulation, it has been shown that mainly specific Tregs component is responsible for the suppressive effect in the assays. After separation of the specific Tregs (proliferating) from nonspecific Tregs (non-proliferating), it has been shown that specific Tregs for 9-23 peptide inhibited T effector cells response statistically significantly more compared to non-specific Tregs. This significance concerned both tests in which the responders were polyclonal T effector cells (ANOVA, F=5.3 p=0.031), as well as specific T effector for 9-23 peptide (ANOVA, F=111.84 p=0.0004).

Stronger inhibition was also observed in the case of insulin-specific Tregs compared to non-specific Tregs when responders were effector T cells specific to insulin. Statistical significance of the effect was only observed in some experiments and post hoc analysis but the overall analysis proved statistically insignificant (ANOVA, F=0.31 p=0.56). There were no differences between insulin specific and non-specific Tregs to the polyclonal responders (ANOVA, F=0.0004 p=0.94).

DISCUSSION

The subject of this article is an in vitro method of obtaining antigen-specific T regulatory cells allowing for clinical use of these cells in the treatment of autoimmune diseases such as e.g. multiple sclerosis, rheumatoid arthritis, type 1 diabetes and to inhibit unwanted immune reactions like transplant rejection, allergic reactions and graft versus host disease (GVHD). Today, T regulatory cells used in the treatments are polyclonal what means, they recognize many different antigens and therefore their effectiveness may be limited (Marek-Trzonkowska N 2014) (Trzonkowski P 2013) (Marek-Trzonkowska N 2013) (Marek-Trzonkowska N 2012) (Hoffmann P 2009) (Trzonkowski P 2009) (Di Ianni M 2011) (Bluestone J A 2015) (Stelmaszczyk-Emmel A 2015) (Vignali D A 2008) (Geem D 2015). This method allows targeting Treg lymphocytes to tissues expressing specific antigens and against specific autoreactive lymphocytes responsible for the inflammatory response against specific antigens. The use of antigen-specific Tregs will allow for more precise treatment and reduction of the Treg dose. In consequence it will increase the effectiveness of treatment and reduce possible side effects.

The usefulness of such antigen-specific Treg lymphocytes has been described in animal models, and a few years ago the first attempts to obtain such cells in humans appeared. Initially, it involved rather induced Treg lymphocytes and Tr1 cells, followed by natural Treg lymphocytes. In the case of the Tregs, the methods are based on the use of naturally occurring antigen presenting cells or properly prepared cells from cell lines that present specific antigens. Recently, attempts have also been made to modify genes consisting in the insertion of regulatory receptors to artificial lymphocytes with specificity against a specific antigen (so-called Treg CAR lymphocytes).

The possibility of antigenically specific regulation of the immune response is important from a therapeutic point of view. Physiologically, the immune system recognizes and destroys foreign and dangerous antigens while tolerating its own weavings. Nevertheless, in the case of autoimmune diseases such as, for example, multiple sclerosis (MS), diabetes mellitus type 1 (DM1), psoriasis, systemic lupus erythematosus (SLE) or rheumatoid arthritis (RA), this mechanism is compromised (Senecal V 2015) (Trzonkowski P 2015) (Marek-Trzonkowska N 2012) (Pujol-Autonell I 2013) (Lima XT 2015) (Mu Q 2015) (Orent W 2015). Effector lymphocytes begin to destroy their own organs, treating autoantigens that build their own tissues as foreign. This process leads to irreversible changes. Currently, the treatment of autoimmune diseases is most often reduced to pharmacological immunosuppression and inhibition of inflammatory response. Such therapy, however, turns out to be ineffective over time. Despite the initial improvement, it is not possible to completely stop the progression of the disease, and its interruption is usually associated with exacerbation of the disease. This treatment is also associated with a profound decline in immunity (Gupta S 2012). Therefore, the patient becomes susceptible to infections, which in patients receiving immunosuppressive drugs have a more serious course than healthy people. Nonspecific immunosuppression is also an increase in the risk of cancer development (a higher percentage of cases among patients receiving immunosuppressive drugs) (Andres A 2005) (Rama I 2010).

Antigen-specific regulation of the immune response is also an important issue from the point of view of transpiantology. Organ transplantation is usually a life-saving procedure, but it is associated with the need to constantly take strong immunosuppressive drugs. Discontinuation of therapy is associated with an increase in the immune response against the tissues of the transplanted organ, which in a short time leads to its destruction. The use of immunosuppressive drugs, as in the case of autoimmune diseases, is associated with the occurrence of serious undesirable side effects. In addition, some of this group of drugs, although they protect the transplanted organ from the destructive effects of the patient's immune system, simultaneously have a toxic effect on the transplant or other tissues. An example here are the nephrotoxicity inhibitors of calcineurin (cyclosporin and tacrolimus) used in kidney transplantation (Prókai Á1 2015) or rapamycin, which is used in the recipients of pancreatic islets, which impairs the action of transplanted cells (Zhang N1 2006) (Berney T 2009). The problem of immunosuppression and regulation of the immune response is also closely related to bone marrow transplants. The main difference between organ transplantation and bone marrow transplantation is that in the first medicine attempts to protect the transplanted organ from the destructive effects of the recipient's immune system, while in the second case there is no risk of transplant rejection, but this transplanted marrow is the source of cells that attack the body recipients and may lead to his death (Di Ianni M 2011) (Zhao K 2015). Regardless of the origin of immune system cells attacking the patient's body, the fight against excessive immune response is also reduced to the use of non-specific immunosuppression. In both cases, i.e. allogeneic solid organ transplants and bone marrow hematopoietic cells, alloantigen are strictly defined which stimulate the immune system response and whose action can be regulated by antigen-specific Treg lymphocytes.

In this study we decided to separate in vitro antigen specific T regulatory cells from all polyclonal Tregs using monocytes loaded with antigen as antigen presenting cells (APC). The diagram of the whole of the presented experiments is shown in FIG. 1.

Polyclonal Treg cells with the CD3+CD4+CD25highCD127 phenotype—grown with autologous gamma-irradiated monocytes displaying a specific antigen (for example insulin or peptide 9-23 insulin beta chain) only proliferate when they have specificity for the antigen presented by monocytes.

Many of the antigens have no affinity to Treg lymphocytes (these cells are anergic) or during stimulation phenotype change and loss of their regulatory properties may be occur. Therefore, the conditions under which a co-culture is carried out are important, on the one hand, to lead to the proliferation of specific Treg cells and on the other hand, maintain their regulatory and suppressor properties. Both conditions were met after addition of anti-CD28 and antiCD154 antibodies to the co-cultures, which provided the missing second signal to Treg cells. Treg lymphocytes specific for the presented antigen in the presence of anti-CD28 and antiCD154 antibodies began to proliferate without losing the stability defined as expression of the FoxP3 factor (it even increased the expression of this factor) and activity in functional suppressions (FIGS. 5-7).

The sorting of the pure antigen-specific Tregene lymphocyte population was done using the FACS cell sorter. Sorting was carried out in laboratory conditions (Aria IIu sorter, BDBiosciences) or in clean laboratory conditions with the admission to production of advanced therapy products (INFLUX sorter qualified for good manufacturing practice conditions—GMP). Sorting was possible thanks to prior staining of polyclonal Treg lymphocytes with a fluorescent dye (CFSE or Violet). Treg cells that proliferate in response to the antigen present, i.e. antigen-specific Tregs, begin to dilute/lose the fluorescence intensity, which decreases by about half with each subsequent cell division. Based on such a change in fluorescence, low fluorescent proliferative cells (antigen specific Treg lymphocytes) and high fluorescent non-proliferating cells (non-specific Treg lymphocytes) can be isolated and sorted (FIG. 2). Such sorted cells can be further grown and used in functional tests.

Presented method allows to obtain antigen-specific Treg lymphocytes that have a preserved regulatory cell phenotype confirmed by the expression of the FoxP3 transcription factor and their activity in functional assays (inhibition of proliferation and inhibition of interferon γ production) is higher than the activity of the starting polyclonal T cell population.

It should be emphasized that the obtained results do not indicate high clonality of the obtained specific cells. The analysis of the TCR repertoire did not show a significant increase in the percentage of Treg lymphocytes expressing a particular class of TCR receptors (FIG. 5).

High expression of FoxP3 (FoxP3$^{High}$) may explain superior suppressor properties of antigen-specific Treg lymphocytes compared to polyclonal Treg lymphocytes. It is well known that FoxP3$^{High}$ cells are the most active suppressor Treg cells fraction because the immunoregulatory activity of them correlates positively with the intensity of expression of FoxP3 factor (Marek N 2011) (Ryba M 2011). The fact that antigen specificity induces a high percentage of FoxP3$^{High}$ cells explains the higher efficacy of therapy in which such cells are used. It seems that the cells are activated only with a specific antigen, and their action is limited to the tissues in which this antigen is expressed. In the functional tests we analyzed the influence of Treg cells on proliferation and on the production of interferon γ (IFN-γ) by T effector lymphocytes. Obtained results indicate that antigen-specific Treg lymphocytes tend to inhibit Teff lymphocyte proliferation and IFN-γ production by these cells in comparison with polyclonal Treg lymphocytes (FIGS. 5-7). This inhibition refers to both polyclonal Teff lymphocytes (FIG. 5*a*, 6*a*, 7) as well as antigen specific Teff lymphocytes (FIG. 5*b*, 6*b*, 7) with respect to the same antigens as the Tregs used during tests. This system is especially important because it's implicate the situation in vivo during the disease, where antigen-specific Teff lymphocytes (autoreactive lymphocytes) are mainly responsible for the destruction of tissues in the autoimmune process or organ rejection.

The fact that the antigen-specific Tregs lymphocytes created by us are able to inhibit specific lymphocytes should have a significant impact on the effectiveness of therapy.

CONCLUDING REMARKS

Using this method we are able to produce antigen specific T regulatory cells. Monocytes used in protocol are loaded with specific antigen. Use of a combination of anti-CD28 and anti-CD154 antibodies to activate the proliferation of antigen-specific Treg lymphocytes stimulated with autologous monocytes discharged with antigen

AUTHOR CONTRIBUTIONS

DI-G, MG and PT wrote the article. PT designed and planned experiments. DI-G, MG and PT performed and analyzed experiments.

FUNDING

This work has been supported by National Centre for Research and Development, Poland: LIDER/160/L-6/14/NCBR/2015 and STRATEGMED 1/233368/1/NCBR/2014 and Polish Ministry of Infrastructure programme POIR.01.01.01-00-0769/15-01 for PolTreg S.A.

ABBREVIATIONS

A FACTT, a European network action to focus and accelerate cell-based tolerance-inducing therapies; Ag, antigen; APC, antigen presenting cells; CFSE, carboxyfluorescein diacetate succinimidyl ester; COST, European Cooperation in Science and Technology; ELISA, enzyme-linked immunosorbent assay; ELISpot, enzyme-linked immunospot; IFN-γ, interferon γ; INS, insulin; Mo, monocytes; NON, non-proliferating (not specific); PBMCs, peripheral blood mononuclear cells; POLY, polyclonal; p/s, penicillin-streptomycin; PRO, proliferating (antigen specific); Tregs, T regulatory cells; Teffs, T effector cells (responders); T1D, type 1 diabetes

REFERENCES

Andres A (2005). "Cancer incidence after immunosuppressive treatment following kidney transplantation." *Crit Rev Oncol Hematol* 56(1): 71-85.

Barbaro M P, Spanevello A, Palladino G P, Salerno F G, Lacedonia D, Carpagnano G E, (2014). "Exhaled matrix metalloproteinase-9 (MMP-9) in different biological phenotypes of asthma." *Eur J Intern Med* 25(1): 92-96.

Berney T, Secchi A (2009). "Rapamycin in islet transplantation: friend or foe?" *Transpl Int* 22(2): 153-161.

Bluestone J A, Buckner J H, Fitch M, Gitelman S E, Gupta S, Hellerstein M K, Herold K C, Lares A, Lee M R, Li K, Liu W, Long S A, Masiello L M, Nguyen V, Putnam A L, Rieck M, Sayre P H, Tang Q, (2015). "Type 1 diabetes immunotherapy using polyclonal regulatory T cells." *Sci Transl Med* 7(315): 315ra189.

Bluestone J A, Trotta E, Xu D, (2015). "The therapeutic potential of regulatory T cells for the treatment of autoimmune disease." *Expert Opin Ther Targets* 19(8): 1091-1103.

Di Ianni M, Falzetti F, Carotti A, Terenzi A, Castellino F, Bonifacio E, Del Papa B, Zei T, Ostini R I, Cecchini D, Aloisi T, Perruccio K, Ruggeri L, Balucani C, Pierini A, Sportoletti P, Aristei C, Falini B, Reisner Y, Velardi A, Aversa F, Martelli M F, (2011). "Tregs prevent GVHD and promote immune reconstitution in HLA-haploidentical transplantation." *Blood* 117(14): 3921-398.

Fontenot J D, Gavin M A, Rudensky A Y, (2003). "Foxp3 programs the development and function of CD4+CD25+ regulatory T cells." *Nat Immunol* 4(4): 330-336.

Gambineri E, Torgerson T R, Ochs H D, (2003). "Immune dysregulation, polyendocrinopathy, enteropathy, and X-linked inheritance (IPEX), a syndrome of systemic autoimmunity caused by mutations of FOXP3, a critical regulator of T-cell homeostasis." *Curr Opin Rheumatol* 15: 430-435.

Geem D, Harusato A, Flannigan K, Denning T L, (2015). "Harnessing regulatory T cells for the treatment of inflammatory bowel disease." Inflamm Bowel Dis 21(6): 1409-1418. Gupta S, (2012). "Immunotherapies in diabetes mellitus type 1." *Med Clin North Am* 96(3): 621-634.

Hoffmann P, Boeld T J, Eder R, Huehn J, Floess S, Wieczorek G, Olek S, Dietmaier W, Andreesen R, Edinger M, (2009). "Loss of FOXP3 expression in natural human CD4+CD25+ regulatory T cells upon repetitive in vitro stimulation." *Eur J Immunol* 39(4): 1088-1097.

Krzystyniak A, Golab K, Witkowski P, Trzonkowski P, (2014). "Islet cell transplant and the incorporation of Tregs." *Curr Opin Organ Transplant* 19(6): 610-615.

Lima X T, Cintra M L, Piaza A C, Mamoni R L, Oliveira R T, Magalhaes R F, Blotta M H, (2015). "Frequency and characteristics of circulating CD4(+) CD28(null) T cells in patients with psoriasis." *Br J Dermatol* 173(4): 998-1005.

Malek T R (2003). "The main function of IL-2 is to promote the development of T regulatory cells." *J Leukoc Biol* 74(6): 961-965.

Malek T R, Castro I (2010). "Interleukin-2 receptor signaling: at the interface between tolerance and immunity." *Immunity* 33(2): 153-165.

Marek-Trzonkowska N, Mysliwiec M, Dobyszuk A, Grabowska M, Techmanska I, Juscinska J, Wujtewicz M A, Witkowski P, Mlynarski W, Balcerska A, Mysliwska J, Trzonkowski P, (2012). "Administration of CD4+ CD25highCD127-regulatory T cells preserves (3-cell function in type 1 diabetes in children." *Diabetes Care* 35(9): 1817-1820.

Marek-Trzonkowska N, My§ liwec M, Siebert J, Trzonkowski P, (2013). "Clinical application of regulatory T cells in type 1 diabetes." *Pediatr Diabetes* 14(5): 322-332.

Marek-Trzonkowska N, Mysliwiec M, Dobyszuk A, Grabowska M, Derkowska I, Jukinska J, Owczuk R, Szadkowska A, Witkowski P, Mlynarski W, Jarosz-Chobot P, Bossowski A, Siebert J, Trzonkowski P, (2014). "Therapy of type 1 diabetes with CD4(+)CD25(high) CD127-regulatory T cells prolongs survival of pancreatic islets—results of one year follow-up." *Clin Immunol* 153(1): 23-30.

Marek N, Bieniaszewska M, Krzystyniak A, Jukinska J, Mysliwska J, Witkowski P, Hellmann A, Trzonkowski P, (2011). "The time is crucial for ex vivo expansion of T regulatory cells for therapy." *Cell Transplant* 20(11-12): 1747-1758.

Martelli M F, Di Ianni M, Ruggeri L, Falzetti F, Carotti A, Terenzi A, Pierini A, Massei M S, Amico L, Urbani E, Del Papa B, Zei T, lacucci Ostini R, Cecchini D, Tognellini R, Reisner Y, Aversa F, Falini B, Velardi A, (2014). "HLA-haploidentical transplantation with regulatory and conventional T-cell adoptive immunotherapy prevents acute leukemia relapse." *Blood* 124(4): 638-644.

Mu Q, Zhang H, Luo X M, (2015). "SLE: another autoimmune disorder influenced by microbes and diet?" *Front Immunol* 6(artykul 608): 1-10.

Nishimura E, Sakihama T, Setoguchi R, Tanaka K, Sakaguchi S, (2004). "Induction of antigen-specific immunologic tolerance by in vivo and in vitro antigen-specific expansion of naturally arising Foxp3+CD25+CD4+ regulatory T cells." *Int Immunol* 16(8): 1189-1201.

Orent W, McHenry A R, Rao D A, White C, Klein H U, Bassil R, Srivastava G, Replogle J M, Raj T, Frangieh M, Cimpean M, Cuerdon N, Chibnik L, Khoury S J, Karlson E W, Brenner M B, De Jager P, Bradshaw E M, Elyaman W, (2015). "Rheumatoid arthritis-associated RBPJ polymorphism alters memory CD4+ T cells." *Hum Mol Genet* DOI: 10.1093/hmg/ddv474.

Panettieri R A, Jr Covar R, Grant E, Hillyer E V, Bacharier L, (2008). "Natural history of asthma: persistence versus progression-does the beginning predict the end?" *J Allergy Clin Immunol* 121(3): 607-613.

Prokai A, Csohany R, Sziksz E, Pap D, Balicza-Himer L, Boros S, Magda B, Vannay Á, Kis-Petik K, Fekete A, Peti-Peterdi J, SzabO AJ, (2015). "Calcineurin-inhibition results in upregulation of local renin and subsequent vascular endothelial growth factor production in renal collecting ducts." *Transplantation* DOI: 10.1097/TP.0000000000000961.

Pujol-Autonell I, Ampudia R M, Monge P, Lucas A M, Carrascal J, Verdaguer J, Vives-Pi M, (2013). "Immunotherapy with Tolerogenic Dendritic Cells Alone or in Combination with Rapamycin Does Not Reverse Diabetes in NOD Mice." *ISRN Endocrinol* 2013(ID 346987): 1-5.

Rama I, Grinyó J M (2010). "Malignancy after renal transplantation: the role of immunosuppression." *Nat Rev Nephrol* 6(9): 511-519.

Ryba M, Marek N, Hak Ł, Rybarczyk-Kapturska K, Myśliwiec M, Trzonkowski P, Myśliwska J, (2011). "Anti-TNF rescue CD4+Foxp3+ regulatory T cells in patients with type 1 diabetes from effects mediated by TNF." *Cytokine* 55(3): 353-361.

Sénécal V, Deblois G, Beauseigle D, Schneider R, Brandenburg J, Newcombe J, Moore C S, Prat A, Antel J, Arbour N, (2015). "Production of IL-27 in multiple sclerosis lesions by astrocytes and myeloid cells: Modulation of local immune responses." *Glia* DOI: 10.1002/glia.22948.

Stelmaszczyk-Emmel A (2015). "Regulatory T cells in children with allergy and asthma: it is time to act." *Respir Physiol Neurobiol* 209: 59-63.

Tang Q, Bluestone JA (2013). "Regulatory T-cell therapy in transplantation-moving to the clinic." *Cold Spring Harb Perspect Med* 3(11): pii: a015552.

Trzonkowski P, Bacchetta R, Battaglia M, Berglund D, Bohnenkamp H R, ten Brinke A, Bushell A, Cools N, Geissler E K, Gregori S, Marieke van Ham S, Hilkens C, Hutchinson J A, Lombardi G, Madrigal J A, Marek-Trzonkowska N, Martinez-Caceres E M, Roncarolo M G, Sanchez-Ramon S, Saudemont A, Sawitzki B, (2015). "Hurdles in therapy with regulatory T cells." *Sci Transl Med* 7(304): 304ps 18.

Trzonkowski P, Bieniaszewska M, Jukiliska J, Dobyszuk A, Krzystyniak A, Marek N, Myś liwska J, Hellmann A, (2009). "First-in-man clinical results of the treatment of patients with graft versus host disease with human ex vivo expanded CD4+CD25+CD127− T regulatory cells." *Clin Immunol* 133(1): 22-26.

Trzonkowski P, Dukat-Mazurek A, Bieniaszewska M, Marek-Trzonkowska N, Dobyszuk A, Juścińska J, Dutka M, My§ liwska J, Hellmann A, (2013). "Treatment of graft-versus-host disease with naturally occurring T regulatory cells." *BioDrugs* 27(6): 605-614.

Trzonkowski P, Szaryfiska M, Mygliwska J, My§ liwski A, (2009). "Ex vivo expansion of CD4(+)CD25(+) T regulatory cells for immunosuppressive therapy." *Cytometry A* 75(3): 175-188.

Vignali D A, Collison L W, Workman C J, (2008). "How regulatory T cells work." *Nat Rev Immunol* 8(7): 523-532.

Wang Y M, Zhang G Y, Wang Y, Hu M, Wu H, Watson D, Hori S, Alexander I E, Harris D C, Alexander S I, (2006). "Foxp3-transduced polyclonal regulatory T cells protect against chronic renal injury from adriamycin." *J Am Soc Nephrol* 17(3): 697-706.

Xiao F, Ma L, Zhao M, Huang G, Mirenda V, Dorling A, Lechler R, Lombardi G, (2014). "Ex vivo expanded human regulatory T cells delay islet allograft rejection via inhibiting islet-derived monocyte chemoattractant protein-1 production in CD34+ stem cells-reconstituted NOD-scid IL2rγnull mice." *PLoS One.* 2014 *Mar.* 3; 9(3):e90387. 9(3)::e9038.

Yi S, Ji M, Wu J, Ma X, Phillips P, Hawthorne W J, O'Connell P J, (2012). "Adoptive transfer with in vitro expanded human regulatory T cells protects against porcine islet xenograft rejection via interleukin-10 in humanized mice." *Diabetes* 61(5): 1180-1191

Zhang N, Su D, Qu S, Tse T, Bottino R, Balamurugan A N, Xu J, Bromberg J S, Dong H H, (2006). "Sirolimus is associated with reduced islet engraftment and impaired beta-cell function." *Diabetes* 55(9): 2429-2436.

Zhao K, Ruan S, Yin L, Zhao D, Chen C, Pan B, Zeng L, Li Z, Xu K, (2015). "Dynamic regulation of effector IFN-γ-producing and IL-17-producing T cell subsets in the development of acute graft-versus-host disease." *Mol Med Rep* 2016 February; 13(2):1395-403.

The invention claimed is:

1. A process for ex-vivo expansion of antigen-specific $CD4^{+}CD25highCD127^{-}$/low T regulatory lymphocytes comprising the steps of:

a) Suspend $CD4^{+}CD25highCD127^{-}$/low T regulatory lymphocytes (Tregs) in PBS containing a fluorescent dye to produce intracellularly stained Tregs;

b) Incubate the stained Tregs in the dark;

c) Wash the stained Tregs several times with culture medium;

d) Suspend the stained Tregs in culture medium and contact with gamma-irradiated autologous CD $14^{+}$ monocytes loaded with antigen to produce a co-culture;

e) Incubate the co-culture with anti-CD154 and anti-CD28 antibodies; and f) Sort the antigen-specific Tregs based on the low intensity of intracellular dye; and the unspecific Tregs based on preserved high fluorescence of the intracellular dye.

2. The process of claim 1 characterized in that the Tregs are suspended in PBS at a concentration of $1\times10^{6}$ cells/ml.

3. The process of claim 1 characterized in that the Tregs are stained with Violet Blue in the final concentration of 1-5 μM.

4. The process of claim 1 characterized in that the final monocyte: Tregs ratio is 1:1.

5. The process of claim 1 characterized in that in step (e) the final concentration of anti-CD154 antibodies is 5 μg/ml and the final concentration of anti-CD28 antibodies is 5 μg/ml.

6. The process of claim 1 further comprising the step of:

a) Characterizing the specificity of Tregs to antigen using a functional test, wherein the functional test comprises assessing the ability of Tregs to suppress the function of T effector lymphocytes.

* * * * *